United States Patent
Mantripragada et al.

(10) Patent No.: US 10,268,198 B2
(45) Date of Patent: Apr. 23, 2019

(54) SYSTEM AND METHOD FOR TRACKING POLLUTION

(71) Applicant: International Business Machines Corporation, Armonk, NY (US)

(72) Inventors: Kiran Mantripragada, São Paulo (BR); Ulisses Mello, Yorktown Heights, NY (US); Rafael Horschutz Nemoto, São Paulo (BR); Nicole Barbosa Sultanum, São Paulo (BR); Lucas Correia Villa Real, São Paulo (BR)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/840,470

(22) Filed: Dec. 13, 2017

(65) Prior Publication Data

US 2018/0101175 A1     Apr. 12, 2018

Related U.S. Application Data

(62) Division of application No. 14/966,038, filed on Dec. 11, 2015, now abandoned.

(51) Int. Cl.
*G05D 1/02*     (2006.01)
*G01N 29/44*    (2006.01)
(Continued)

(52) U.S. Cl.
CPC .......... *G05D 1/0212* (2013.01); *G01N 29/02* (2013.01); *G01N 29/4454* (2013.01);
(Continued)

(58) Field of Classification Search
CPC .............. G01N 29/02; G01N 33/0036; G01N 33/0067; G01N 29/4454; G01N 2291/021;
(Continued)

(56) References Cited

U.S. PATENT DOCUMENTS 6,104,299 A  *  8/2000  Brusseaux ......... G01N 33/0075
                                                        340/603
7,789,723 B2     9/2010  Dane et al.
(Continued)

FOREIGN PATENT DOCUMENTS

| CN | 102980977 | 3/2013 |
|---|---|---|
| WO | 89/07304 | 8/1989 |

(Continued)

OTHER PUBLICATIONS

A decision-theoretic approach to detection-based target search with a UAV Aayush Gupta; Daniel Bessonov; Patrick Li 2017 IEEE/RSJ International Conference on Intelligent Robots and Systems (IROS); pp. 5304-5309,Year: 2017.*

(Continued)

*Primary Examiner* — Cuong H Nguyen (74) *Attorney, Agent, or Firm* — F. Chau & Associates, LLC (57) ABSTRACT

A pollution source detection system, includes an automated vehicle including a position sensor that detects a geographic position of the automated vehicle and at least one pollution detection sensor that measures a concentration of pollution at the automated vehicle. The pollution source detection system includes a back-end system. The back-end system includes a network interface that receives the geographic position and the concentration of the pollution from the automated vehicle. The back-end system includes a database that stores the geographic position and the concentration of the pollution received via the network interface. The back-end system includes a processor that measures a gradient of the concentration of the pollution and controls a movement of the automated vehicle based on the gradient to guide the automated vehicle toward a source of the pollution.

15 Claims, 7 Drawing Sheets

(51) Int. Cl.
G01N 33/00 (2006.01)
G01N 29/02 (2006.01)
G05D 1/10 (2006.01)

(52) U.S. Cl.
CPC ..... *G01N 33/0036* (2013.01); *G01N 33/0067* (2013.01); *G05D 1/0291* (2013.01); *G05D 1/104* (2013.01); *G01N 2291/021* (2013.01); *G05D 2201/0207* (2013.01)

(58) Field of Classification Search
CPC .... G05D 1/104; G05D 1/0212; G05D 1/0291; G05D 2201/0207
USPC ................................ 701/24; 73/23.35, 23.38
See application file for complete search history.

(56) References Cited

U.S. PATENT DOCUMENTS

| | | | |
|---|---|---|---|
| 8,269,971 B1 | 9/2012 | Marsh et al. | |
| RE44,214 E | 5/2013 | Peterson et al. | |
| 8,560,146 B2 | 10/2013 | Kwon et al. | |
| 8,730,461 B2 | 5/2014 | Andreussi | |
| 8,903,646 B2 | 12/2014 | Althen et al. | |
| 2004/0090628 A1* | 5/2004 | Ershov | G01N 21/031 356/438 |
| 2005/0222933 A1* | 10/2005 | Wesby | G06Q 40/00 705/36 R |
| 2010/0265329 A1 | 10/2010 | Doneker | |
| 2011/0208414 A1 | 8/2011 | Althen et al. | |
| 2011/0251800 A1 | 10/2011 | Wilkins | |
| 2012/0271561 A1 | 10/2012 | Keller-Goralczyk et al. | |
| 2013/0144527 A1 | 6/2013 | Kuhnreich | |
| 2013/0278427 A1 | 10/2013 | Setton | |
| 2014/0077969 A1 | 3/2014 | Vian et al. | |
| 2015/0286785 A1* | 10/2015 | Hielscher | A61B 5/0073 382/131 |
| 2017/0076509 A1* | 3/2017 | Scofield | G08G 1/0112 |
| 2017/0168487 A1 | 6/2017 | Mantripragada et al. | |

FOREIGN PATENT DOCUMENTS

| | | |
|---|---|---|
| WO | 98/16421 | 4/1998 |
| WO | 2012/046180 | 4/2012 |

OTHER PUBLICATIONS

Software Defined Networks (SDNs) of RF Internet of Things (RIOTs) on Unmanned Aerial Systems (UASs) William D. Watson; Steve Huntsman; James T. Dolan MILCOM 2017—2017 IEEE Military Communications Conference (MILCOM); Year: 2017; pp. 291-296; IEEE Conferences.*
Anti-saturation and contrast enhancement technique using interlaced histogram equalization (IHE) for improving target detection performance of EO/IR images;Byeong Hak Kim; Min Young Kim; 2017 17th International Conference on Control, Automation and Systems (ICCAS); Year: 2017; pp. 1692-1695; IEEE Conferen.*
Michael A. Kovacina, et al., "Multi-Agent Control Algorithms for Chemical Cloud Detection and Mapping Using Unmanned Air Vehicles," Proceedings of the 2002 IEEE/RSJ, International Conference on Intelligent Robots and Systems, EPFL, Lausanne, Switzerland, Oct. 2002, pp. 2782-2788.
Vaclav Smidl, et al., "Tracking of Atmospheric Release of Pollution Using Unmanned Aerial Vehicles," Atmospheric Environment 67 (2013) pp. 425-436.
John Oyekan, et al., "A Novel Bio-Controller for Localizing Pollution Sources in a Medium Peclet Environment," Journal of Bionic Engineering 7 (2010) pp. 345-353.
Liqian Peng, et al., "Sensor Driven Feedback for Puff Estimation Using Unmanned Aerial Vehicles," 2014 International Conference on Unmanned Aircraft Systems (ICUAS) May 27-30, 2014, pp. 562-569.
Kochanski, Adam K., et al., "Air pollution forecasting by coupled atmosphere-fire model WRF and SFIRE with WRF-Chem." arXiv preprint arXiv:1304.7703(2013).
Pielke, Roger A., et al. "The use of a mesoscale numerical model for evaluations of pollutant transport and diffusion in coastal regions and over irregular terrain." Bulletin of the American Meteorological Society 64.3 (1983): 243-249.
Watanabe, T., K. Asai, and A. Houki. "Numerical estimation to organic pollution of flowing water by using the epilithic diatom assemblage—diatom assemblage index (DAI po)—," Science of the total environment 55 (1986): 209-218.
Rajkovic, Borivoj, Zoran Grsic, and Mirjam Vujadinovic. "Detection of a Possible Source of Air Pollution Using a Combination of Measurements and Inverse Modelling." Air Pollution Modeling and Its Application XIX. Springer Netherlands, 2008. 689-690.
Stockton, Gregory R. "Finding pollution with aerial infrared thermography." Industrial Physicist 10.2 (2004): 24-27.
Melendez-Pastor, I., et al. "The Use of Remote Sensing to Locate Heavy Metal as Source of Pollution." Advances in Environmental Research, vol. 7, (2011) pp. 225-233.
Wang, Qinggai, et al. "A review of surface water quality models." The Scientific World Journal 2013 (2013).
Thompson, Richard M. "Drones in domestic surveillance operations: Fourth amendment implications and legislative responses." Congressional Research Service, Library of Congress, 2012.
Rowe, Jonathan E., and Michael D. Vose. "Unbiased black box search algorithms." Proceedings of the 13th annual conference on Genetic and evolutionary computation. ACM, 2011.
Adi, Delint Ira Setyo, Siti Mariyam Shamsuddin, and Aida Ali, "Particle Swarm Optimization for NURBS curve fitting." Computer Graphics, Imaging and Visualization, 2009. CGIV'09, Sixth International Conference on. IEEE, 2009.
Peter Finn, "Domestic Use of Aerial Drones by Law Enforcement Likely to Prompt Privacy Debate," Washington Post, Article, Jan. 23, 2011, pp. 1-6.
Andy Pasztor, et al., "Drone Use Takes Off on the Home Front," Wall Street Journal, Article, Apr. 21, 2012, pp. 1-3.
Matrix-Based Multigrid Numerical Methods and Algorithms, vol. 2—Chapter: The Multigrid Iteration. 2008, pp. 109-129.
Committee on Environment and Natural Resources, and Sustainability of the National Science and Technology Council, "Air Quality Observation Systems in the United States," Nov. 2013, pp. 1-96.
Peter N. Spotts, "Cloud-sniffing drones soar over Asia" published Aug. 27, 2008 [online at the internet:<URL https://www.csmonitor.com/Environment/Global-Warming/2008/0827/cloud-sniffing-drones-soar-over-asia], [Last Visited Nov. 16, 2017].
Department of Physics and Technology, University of Bergen, "RGA—algorithm for black box global optimization" [online at the internet:<URL http://web.ift.uib.no/~antonych/RGA0.html], [Last Visited Nov. 16, 2017].
Environmental Protection Agency, "Multi-scale Modeling of the Effects of Global Change upon Regional Air Quality" published Sep. 2, 2015 [online at the internet:<URL https://archive.epa.gov/ncer/events/calendar/archive/web/pdf/lamb_presentation.pdf]. [Last Visited Nov. 16, 2017].
Fast Company, "These Beautiful Smart Kites Detect Air Pollution" published Jul. 12, 2012 [online at the internet:<URL https://www.fastcompany.com/1680156/these-beautiful-smart-kites-detect-air-pollution]. [Last Visited Nov. 16, 2017].
Wicked Device, "Air Quality Egg—What is the Egg?" [online at the internet<URL h http://airqualityegg.com/], [Last Visited Nov. 16, 2017].
National Centre for Computational Hydroscience and Engineering, "Water Quality Modeling" [online at the internet: <URL http://www.ncche.olemiss.edu/research/basic/water]. [Last Visited Jun. 29, 2015].
U.S. Environmental Protection Agency, "Dispersion Modeling" [online at the internet<URL http://www.epa.gov/ttn/scram/dispersionindex.htm]. [Last Visited Jun. 1, 2015].
G. Nan, et al., "Tunable diode laser absorption spectroscopy for sensing CO and $CO_2$ of vehicle emissions based on temperature (56) References Cited

OTHER PUBLICATIONS tuning", 2011 International Conference on Business Management and Electronic Information, Year: 2011, vol. 4, pp. 853-856.

A. B. Gadkari, et al., "Ferrite Gas Sensors", IEEE Sensors Journal, vol. 11, No. 4, Apr. 2011, pp. 849-861.

R. Mraihi, et al., "Sustainable transport in Tunisia: an analysis of the environmental Kuznets curve", 2013 International Conference on Advanced Logistics and Transport; Year: 2013; pp. 30-34.

Dr. A.-R. Diercks, et al., "NIUST—Deepwater Horizon Oil Spill Response Cruise", Oceans 2010 MTS/IEEE Seattle, Year: 2010; pp. 1-7.

\* cited by examiner

SYSTEM AND METHOD FOR TRACKING POLLUTION

CROSS-REFERENCE TO RELATED APPLICATION

This application is a divisional of U.S. application Ser. No. 14/966,038, filed on Dec. 11, 2015, the disclosure of which is incorporated by reference herein in its entirety.

BACKGROUND

Exemplary embodiments of the present invention relate to tracking pollution. More particularly, exemplary embodiments of the present invention relate to a system and method for tracking pollution by determining pollution concentration gradients with unmanned vehicles.

Generally, pollution, such as air, water, soil or noise pollution, may be detected using manual instrumentation that is operated by individual human operators in an area expected to have pollution. Pollution detection equipment may also be mounted at fixed positions in different locations or geographic areas. Pollution may be emitted from a wide array of locations and the pollution may spread over a large geographic area. Spreading pollution may be present at a large range of concentrations in different areas. Pollution may also spread according to patterns that are not readily predicted, such as according to shifting wind patterns or shifting water currents. Thus, pollution detection equipment may be disposed in fixed positions over a wide geographic area to detect pollution emitted from a single source. For example, emissions from industrial equipment or a power plant may travel relatively large distances according to wind patterns and pollution emitted from such a source may be present at varying concentrations at varying distances from the emission source.

Pollution may be detected at relatively low concentrations in a particular geographic area and the source of the detected solution may be unknown. Thus, it may be desirable to have pollution detection equipment present over a large geographic area to determine pollution concentrations in different areas to determine an origin or source of a particular form of pollution.

SUMMARY

Exemplary embodiments of the present invention provide a pollution source detection system including an automated vehicle including a position sensor that detects a geographic position of the automated vehicle and at least one pollution detection sensor that measures a concentration of pollution at the automated vehicle. The pollution source detection system includes a back-end system. The back-end system includes a network interface that receives the geographic position and the concentration of the pollution from the automated vehicle. The back-end system includes a database that stores the geographic position and the concentration of the pollution received via the network interface. The back-end system includes a processor that measures a gradient of the concentration of the pollution and controls a movement of the automated vehicle based on the gradient to guide the automated vehicle toward a source of the pollution.

According to an exemplary embodiment of the present invention the processor may measure the gradient using a numerical model.

According to an exemplary embodiment of the present invention the processor may measure the gradient in real-time as the automated vehicle moves.

According to an exemplary embodiment of the present invention the pollution source detection system may include a plurality of automated vehicles including the automated vehicle. Each of the plurality of automated vehicles may include a position sensor that detects a geographic position of the corresponding automated vehicle and at least one pollution detection sensor that measures a concentration of pollution at the corresponding automated vehicle. The processor may aggregate the concentration of the pollution measured by the plurality of automated vehicles, measure an aggregated gradient of the aggregated concentration of the pollution, and control a movement of the plurality of automated vehicles based on the aggregated gradient to guide the plurality of automated vehicles toward the source of the pollution.

According to an exemplary embodiment of the present invention at least one pollution detection sensor may include a microphone. The pollution may include noise pollution, and the microphone may detect the concentration of the noise pollution.

According to an exemplary embodiment of the present invention at least one of the pollution sensors may include an air quality sensor. The pollution may include air pollution. The air quality sensor may detect a concentration of the air pollution by detecting a concentration of at least one of $O_3$, $NO_2$, $CO$, $SO_2$, PM10, PM2.5 and $C_6H_6$.

According to an exemplary embodiment of the present invention at least one of the pollution detection sensors may include a camera, a hyperspectral sensor, an ultrasound sensor, a thermal sensor, a humidity sensor, a temperature sensor, a pressure sensor, or a corrosion sensor.

According to an exemplary embodiment of the present invention the position sensor may include a GPS sensor.

According to an exemplary embodiment of the present invention the position sensor may detect the geographic position in three dimensions.

According to an exemplary embodiment of the present invention the automated vehicle may be an automated air vehicle that moves through air without contacting ground, an automated ground vehicle that moves on the ground while contacting the ground, or an automated water vehicle that moves in water.

According to an exemplary embodiment of the present invention the network interface may initially receive a general location at which the pollution is present from a source other than the automated vehicle. The processor may subsequently guide the automated vehicle to the general location and may control the movement of the automated vehicle based on the gradient to guide the automated vehicle toward the source of the pollution within the general location.

According to an exemplary embodiment of the present invention the processor may perform an inverse geocoding query to detect a company or individual responsible for the source of the pollution.

Exemplary embodiments of the present invention provide a method of detecting a source of pollution including detecting a geographic position of an automated vehicle by a position sensor disposed on the automated vehicle. A concentration of the pollution is measured by at least one pollution detection sensor disposed on the automated vehicle. The geographic position and the concentration of the pollution are received via a network interface disposed at a back-end system from the automated vehicle. The geographic position and the concentration of the pollution received via the network interface are stored in a database disposed at the back-end system. The method of detection of a source of pollution includes measuring, by a processor disposed at the back-end system, a gradient of the concentration of the pollution. The method of detection of a source of pollution includes controlling, by the processor, a movement of the automated vehicle based on the gradient to guide the automated vehicle toward the source of the pollution.

According to an exemplary embodiment of the present invention the processor may measure the gradient using a numerical model.

According to an exemplary embodiment of the present invention the processor may measure the gradient in real-time as the automated vehicle moves.

According to an exemplary embodiment of the present invention the method of detection of a source of pollution may include detecting a geographic position of each of a plurality of automated vehicles, including the automated vehicle, by a position sensor disposed on each of the plurality of automated vehicles. A concentration of the pollution may be measured by at least one pollution detection sensor disposed on each of the plurality of automated vehicles. The concentration of the pollution measured by the plurality of automated vehicles may be aggregated. An aggregated gradient of the aggregated concentration of the pollution may be measured. A movement of the plurality of automated vehicles may be controlled based on the aggregated gradient to guide the plurality of automated vehicles toward the source of the pollution.

According to an exemplary embodiment of the present invention the method of detection of a source of pollution may include initially receiving a general location at which the pollution is present from a source other than the automated vehicle and subsequently guiding the automated vehicle to the general location. The movement of the automated vehicle may be controlled based on the gradient to guide the automated vehicle toward the source of the pollution within the general location.

According to an exemplary embodiment of the present invention the method of detection of a source of pollution may include performing, by the processor, an inverse geocoding query to detect a company or individual responsible for the source of the pollution.

Exemplary embodiments of the present invention provide a computer program product for detecting a source of pollution. The computer program product may include a computer readable storage medium having program instructions embodied therewith, the program instructions executable by a processor to cause the processor to detect a geographic position of an automated vehicle by a position sensor disposed on the automated vehicle. The program instructions executable by the processor cause the processor to measure a concentration of the pollution by at least one pollution detection sensor disposed on the automated vehicle. The program instructions executable by the processor cause the processor to receive the geographic position and the concentration of the pollution via a network interface disposed at a back-end system from the automated vehicle. The program instructions executable by the processor cause the processor to store the geographic position and the concentration of the pollution received via the network interface in a database disposed at the back-end system. The program instructions executable by the processor cause the processor to measure a gradient of the concentration of the pollution and control a movement of the automated vehicle based on the gradient to guide the automated vehicle toward the source of the pollution.

BRIEF DESCRIPTION OF THE DRAWINGS

The above and other features of the present invention will become more apparent by describing in detail exemplary embodiments thereof, with reference to the accompanying drawings, in which.

DETAILED DESCRIPTION

Exemplary embodiments of the present invention will be described more fully hereinafter with reference to the accompanying drawings. Like reference numerals may refer to like elements throughout the specification and drawings.

Exemplary embodiments of the present invention relate to tracking pollution. Exemplary embodiments of the present invention may provide a system and method for automatically tracking pollution using automated vehicles. More particularly, exemplary embodiments of the present invention relate to a system and method for tracking pollution by tracking gradient concentration with unmanned vehicles.

Pollution may be emitted from a variety of sources and the emitted pollution may spread over a large geographic area. The source of pollution may be a known source, such as a power plant, or an industrial area, or a source of a particular type of solution may be unknown. The emitted pollution may be present at a relatively large range of concentrations. For example, pollution emitted from a particular source may dissipate as distance increases from the emission source. Additionally, concentrations of pollution may vary unevenly with distance from a particular emission source. For example, strong winds in a particular direction may spread air pollution unevenly over a particular geographic area. Thus, concentrations of pollution spreading over a particular geographic area may be difficult to predict and installing or placing emission detection equipment in appropriate locations may be difficult. When the source of pollution is unknown the concentration of the pollution may be useful for detecting the source of the pollution. For example, pollution may be tracked and/or the source of pollution may be determined by tracking the concentration of pollution using automated or unmanned vehicles according to exemplary embodiments of the present invention.

A source of pollution may be a moving source, such as a motorized vehicle. For example, cars, trucks, boats or plains may emit pollution such as air or water pollution and thus the source of this pollution might not be fixed in a specific geographic location. Automated or unmanned vehicles according to exemplary embodiments of the present invention may determine a source of pollution when the source of pollution is such a moving source. The automated or unmanned vehicles according to exemplary embodiments of the present invention may detect the concentration gradient of the pollution emitted from the moving source and may track the emitted pollution by following the concentration gradient toward the mobile pollution source. That is, the automated or unmanned vehicles according to exemplary embodiments of the present invention may continually move toward a higher concentration gradient to identify the mobile pollution source.

Pollution may be in the form of air pollution such as ozone or carbon monoxide which may spread according to wind or air currents. Pollution may also be in the form of noise pollution or water or soil pollution. However, exemplary embodiments of the present invention are not limited to a particular type of pollution and the system and method according to exemplary embodiments of the present invention may identify and track any type of detectable pollution, as desired. Unmanned or automated vehicles may reach substantially any geographic location in terms of latitude, longitude and altitude and pollution may be identified at substantially any geographic location using unmanned or automated vehicles, for example, by detecting and tracking the concentration gradient of the pollution. Geographic locations of pollution sources may be identified in terms of latitude, longitude and altitude. Thus, any desired form of pollution may be tracked, and the source of any desired form of pollution may be identified.

When pollution is noise pollution, the pollution may be in the form of relatively loud or high decibel sound emitted into the environment. In the case of noise, the concentration gradient may be a gradient of higher decibel or relatively louder sound to lower decibel or relatively lower sound. The concentration gradient of sound may be used according to exemplary embodiments of the present invention to identify a source of emitted sound, and thus the sound emitter may be adjusted to reduce the volume of the sound emitted. For example, sound may be emitted at a level which violates a local ordinance or a state or federal law, either knowingly or unknowingly, and identification of the sound source may allow for reduction of the sound to reduce or eliminate noise pollution.

One form of pollution according to an exemplary embodiment of the present invention may be increased temperature pollution. That is, a pollution source may artificially heat a geographic region by emitting heat into the environment. The gradient at any location or geographic point may be combined to direct the automated vehicle in the direction of the higher temperature increase (e.g., the highest gradient of concentration). Thus, the gradient of concentration may be used to direct the automated vehicle toward the pollution source.

Unmanned or automated vehicles according to exemplary embodiments of the present invention may include vehicles traveling on air, water or the ground. For example, vehicles traveling on air may include aerial vehicles such as drones, balloons, planes, helicopters or other aircraft. Vehicles traveling on water may include boats and/or personal watercraft. Vehicles traveling on the ground may include cars, truck or all terrain vehicles, for example. However, exemplary embodiments of the present invention are not limited to a particular type of automated or unmanned vehicle and any desired automated or unmanned vehicle may be used.

Automated vehicles detecting or tracking water pollution according to an exemplary embodiment of the present invention may detect and track water or air pollution on a surface of a body of water or below a surface of the body of water. That is, unmanned or automated vehicles may travel above or below the surface of the body of water. Unmanned or automated vehicles traveling below the surface of water may include submersible vehicles such as submarines. Submersible vehicles according to exemplary embodiments of the present invention may travel to any desired depth and may track pollution at any desired depth.

By identifying a source of pollution according to exemplary embodiments of the present invention, the source of pollution may be modified in any desired way to reduce or eliminate the emission of pollution. For example, a damaged or broken gas or liquid pipe may have an unknown leak which emits pollution. When the source of such pollution is identified the broken pipe may be repaired or replaced to reduce or eliminate the emission of pollution.

Figure 1:
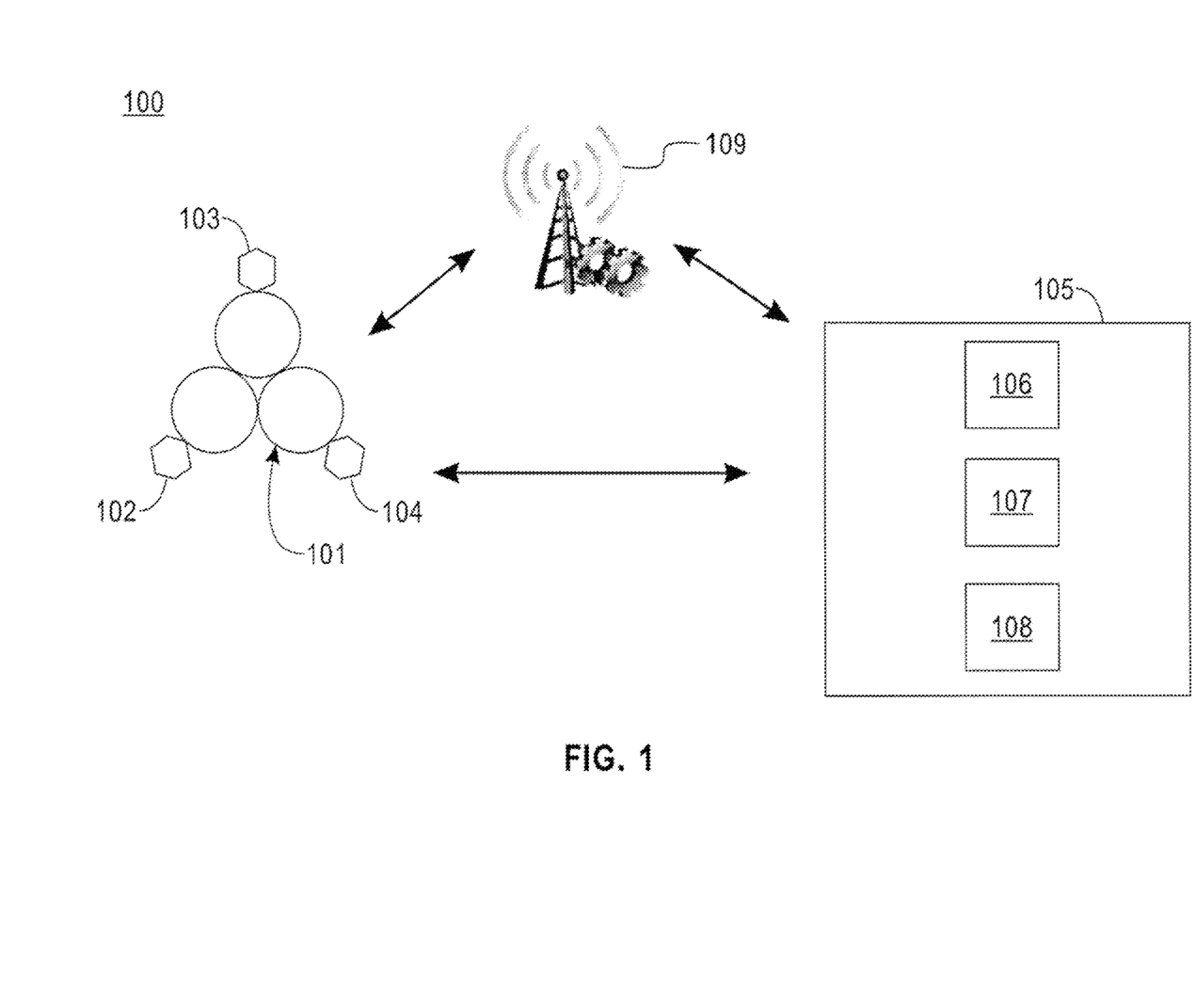
FIG. 1 illustrates an example of a pollution source detection system according to an exemplary embodiment of the present invention.

FIG. 1 illustrates an example of a pollution source detection system according to an exemplary embodiment of the present invention.

Referring to FIG. 1, a pollution source detection system 100 according to an exemplary embodiment of the present invention may include an automated vehicle 101 including a position sensor 102 that detects a geographic position of the automated vehicle 101 and at least one pollution detection sensor 103 that measures a concentration of pollution at the automated vehicle 101. The pollution source detection system 100 may include a back-end system 105. The back-end system 105 may include a network interface 106 that receives the geographic position and the concentration of the pollution from the automated vehicle 101. The back-end system 105 may include a database 107 that stores the geographic position and the concentration of the pollution received via the network interface 106. The back-end system 105 may include a processor 108 that measures a gradient of the concentration of the pollution and controls a movement of the automated vehicle 101 based on the gradient to guide the automated vehicle 101 toward a source of the pollution.

According to an exemplary embodiment of the present invention, the automated vehicle 101 of the pollution source detection system 100 may include a GPS unit 104 (e.g., GPS sensor). According to an exemplary embodiment of the present invention the position sensor 102 may include the GPS unit 104. That is, the UPS unit (e.g., UPS sensor) may be connected to the position sensor 102 or the position sensor 102 may operate as the UPS unit.

The UPS unit 104 may detect a geographic location of the automated vehicle 101. The (IPS unit 104 may detect a latitude, longitude, and/or altitude of the automated vehicle 101. The UPS unit 104 may communicate with one or more satellites to determine the latitude, longitude, and/or altitude of the automated vehicle 101 and the source of the pollution.

The pollution source detection system 100 according to an exemplary embodiment of the present invention may include one or more relay towers 109. The relay towers 109 may communicate with the automated vehicle 101 and may relay a signal from the automated vehicle 101 to the back-end system 105. The relay tower 109 may communicate with the back-end system 105 and may relay a signal from the back-end system 105 to the automated vehicle 101. The automated vehicle 101 may communicate with the back-end system 105 directly without relaying a signal through the relay tower 109.

The relay tower 109 according to exemplary embodiments of the present invention may be a cell phone tower. The relay tower 109 according to exemplary embodiments of the present invention may increase the intensity of a signal transmitted by the automated vehicle 101. Thus, the relay tower 109 according to exemplary embodiments of the present invention may reduce the amount of power consumed by the automated vehicle 101 and may increase the range of the automated vehicle 101.

The back-end system 105 according to an exemplary embodiment of the present invention may be disposed in the automated vehicle 101. For example, back-end system 105 may be disposed in at least one of a plurality of automated vehicles 101 and may communicate with each of the plurality of automated vehicles 101. A plurality of automated vehicles 101 will be described in more detail below.

According to an exemplary embodiment of the present invention the processor 108 may measure the gradient using a numerical model.

According to an exemplary embodiment of the present invention the processor 108 may measure the gradient in real-time as the automated vehicle 101 moves. The gradient may be reported to the back-end system 105 in real-time and the back-end system 105 may communicate with the automated vehicle 101 in real-time.

Figure 2:
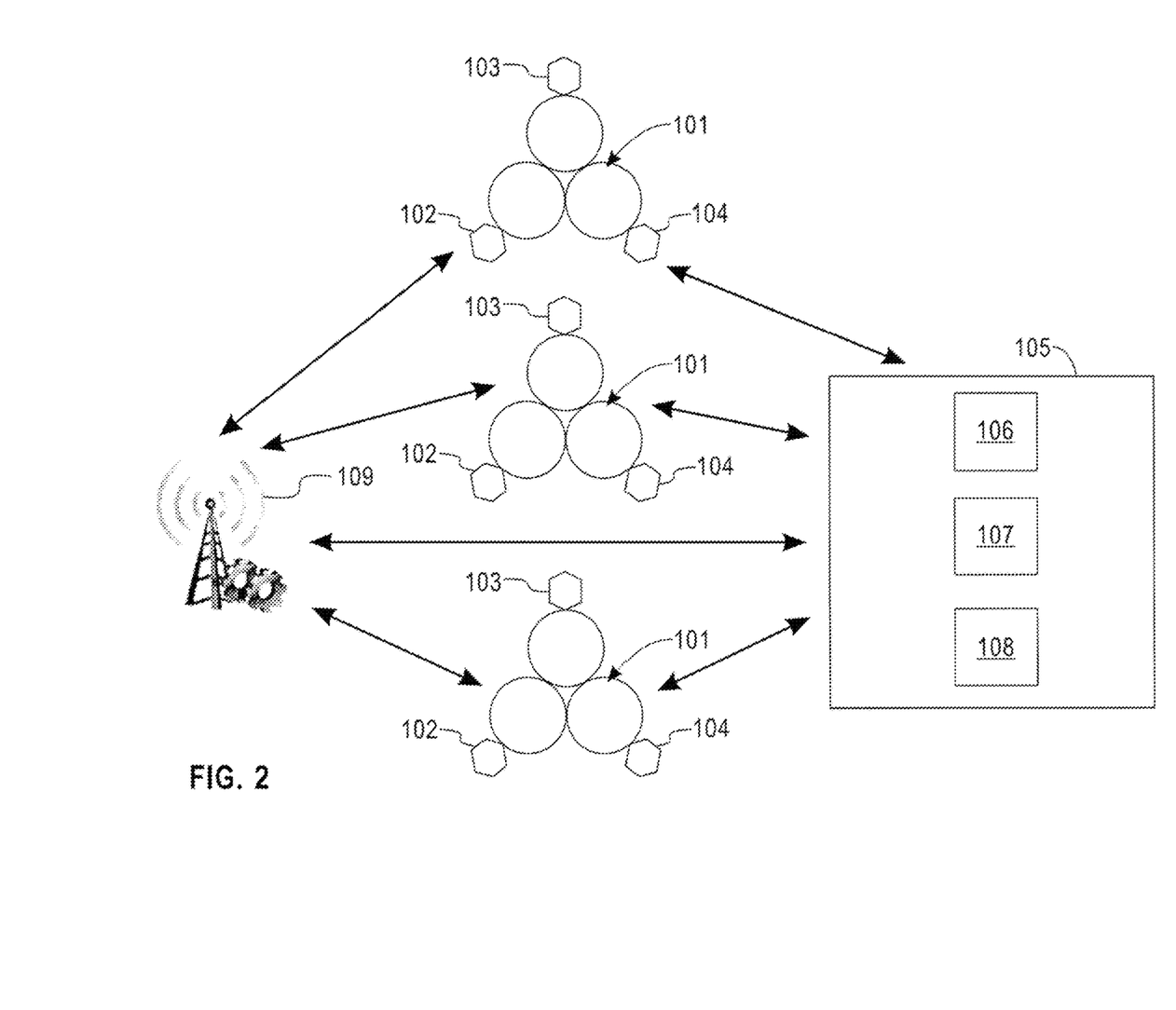
FIG. 2 illustrates an example of a pollution source detection system according to an exemplary embodiment of the present invention.

FIG. 2 illustrates an example of a pollution source detection system according to an exemplary embodiment of the present invention.

Referring to FIG. 2, the pollution source detection system 100 may include a plurality of automated vehicles including the automated vehicle 101. Each of the plurality of automated vehicles 101 may include the position sensor 102 that detects a geographic position of the corresponding automated vehicle 101 and at least one pollution detection sensor 103 that measures a concentration of pollution at the corresponding automated vehicle 101. The processor 108 may aggregate the concentration of the pollution measured by the plurality of automated vehicles 101, measure an aggregated gradient of the aggregated concentration of the pollution, and control a movement of the plurality of automated vehicles 101 based on the aggregated gradient to guide the plurality of automated vehicles 101 toward the source of the pollution.

According to an exemplary embodiment of the present invention at least one pollution detection sensor 103 may include a microphone. The pollution may include noise pollution, and the microphone may detect the concentration of the noise pollution.

According to an exemplary embodiment of the present invention at least one of the pollution sensors 103 may include an air quality sensor. The pollution may include air pollution. The air quality sensor may detect a concentration of the air pollution by detecting a concentration of at least one of $O_3$, $NO_2$, CO, $SO_2$, PM10, PM2.5 and $C_6H_6$. The air quality sensor may detect a concentration of the air pollution by detecting a concentration of at least one of hydrocarbons (HC), nitrogen oxides ($NO_x$), particulate matter (PM), volatile organic compounds (VOCs), hydrogen sulfide ($H_2S$) or other toxic air contaminants such as lead (Pb).

According to an exemplary embodiment of the present invention at least one of the pollution detection sensors 103 may include a camera, a hyperspectral sensor, an ultrasound sensor, a thermal sensor, a humidity sensor, a temperature sensor, a pressure sensor, or a corrosion sensor.

According to an exemplary embodiment of the present invention, each of the automated vehicles 101 of the pollution source detection system 100 may include the UPS unit 104 (e.g., GPS sensor). According to an exemplary embodiment of the present invention the position sensor may include the GPS unit 104. That is, the UPS unit (e.g., UPS sensor) may be connected to the position sensor 102 or the position sensor 103 may operate as the UPS unit.

According to an exemplary embodiment of the present invention the position sensor 102 and/or the UPS unit 104 may detect the geographic position in three dimensions.

The UPS unit 104 may detect a geographic location of each of the automated vehicles 101. The GPS unit 104 may detect a latitude, longitude, and/or altitude of each of the automated vehicle 101. The UPS unit 104 may communicate with one or more satellites to determine the latitude, longitude, and/or altitude of each of the automated vehicles 101.

The pollution source detection system 100 according to an exemplary embodiment of the present invention may include one or more relay towers 109. The relay towers 109 may communicate with the plurality of automated vehicles 101 and may relay a signal from the automated vehicles 101 to the back-end system 105. The relay tower 109 may communicate with the back-end system 105 and may relay a signal from the back-end system 105 to each of the plurality of automated vehicles 101. The plurality of automated vehicles 101 may communicate with the back-end system 105 directly without relaying a signal through the relay tower 109.

The relay tower 109 according to exemplary embodiments of the present invention may be a cell phone tower. The relay tower 109 according to exemplary embodiments of the present invention may increase the intensity of a signal transmitted by each of the automated vehicles 101. Thus, the relay tower 109 according to exemplary embodiments of the present invention may reduce the amount of power consumed by the automated vehicles 101 and may increase the range of the automated vehicles 101.

According to an exemplary embodiment of the present invention the automated vehicle 101 may be an automated air vehicle that moves through air without contacting ground, an automated ground vehicle that moves on the ground while contacting the ground, or an automated water vehicle that moves in water.

According to an exemplary embodiment of the present invention the network interface 106 may initially receive a general location at which the pollution is present from a source other than the automated vehicle 101. The processor 108 may subsequently guide the automated vehicle 101 to the general location and may control the movement of the automated vehicle 101 based on the gradient to guide the automated vehicle 101 toward the source of the pollution within the general location.

According to an exemplary embodiment of the present invention the processor 108 may perform an inverse geocoding query to detect a company or individual responsible for the source of the pollution. That is, the processor 108 may determine an owner of a parcel of land on which pollution is being emitted or an owner of a particular item of equipment emitting pollution.

Figure 3:
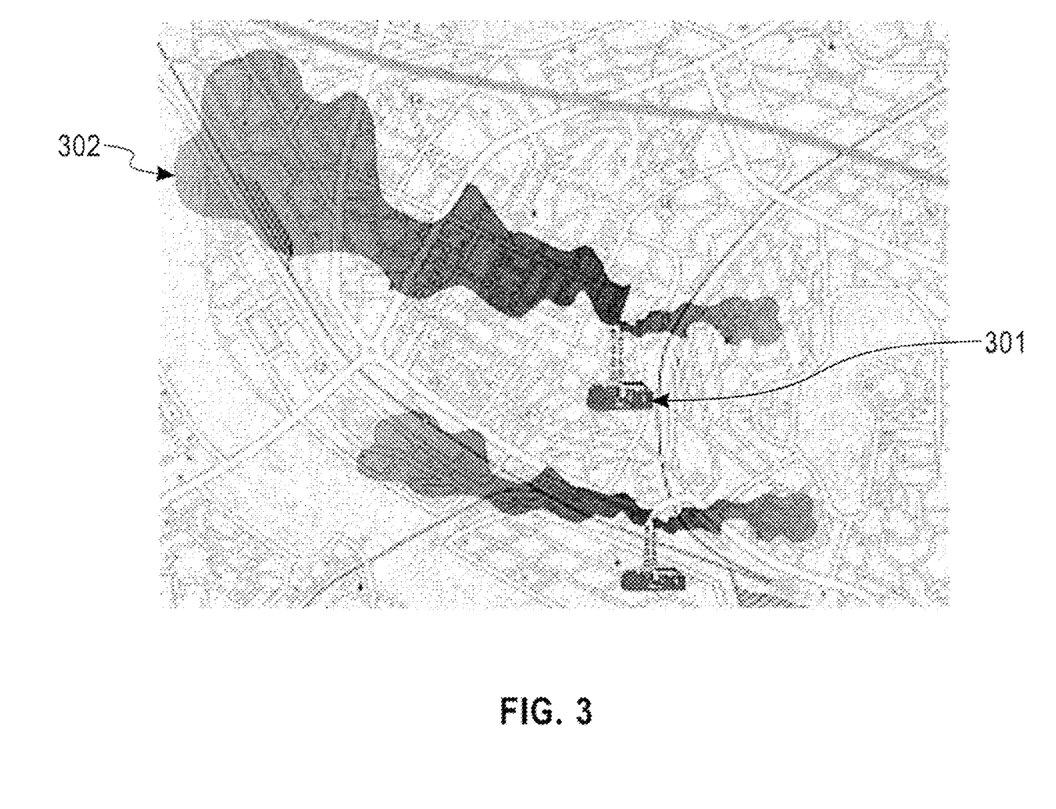
FIG. 3 illustrates an example of a pollution concentration gradient of emitted pollution according to an exemplary embodiment of the present invention.
Figure 4:
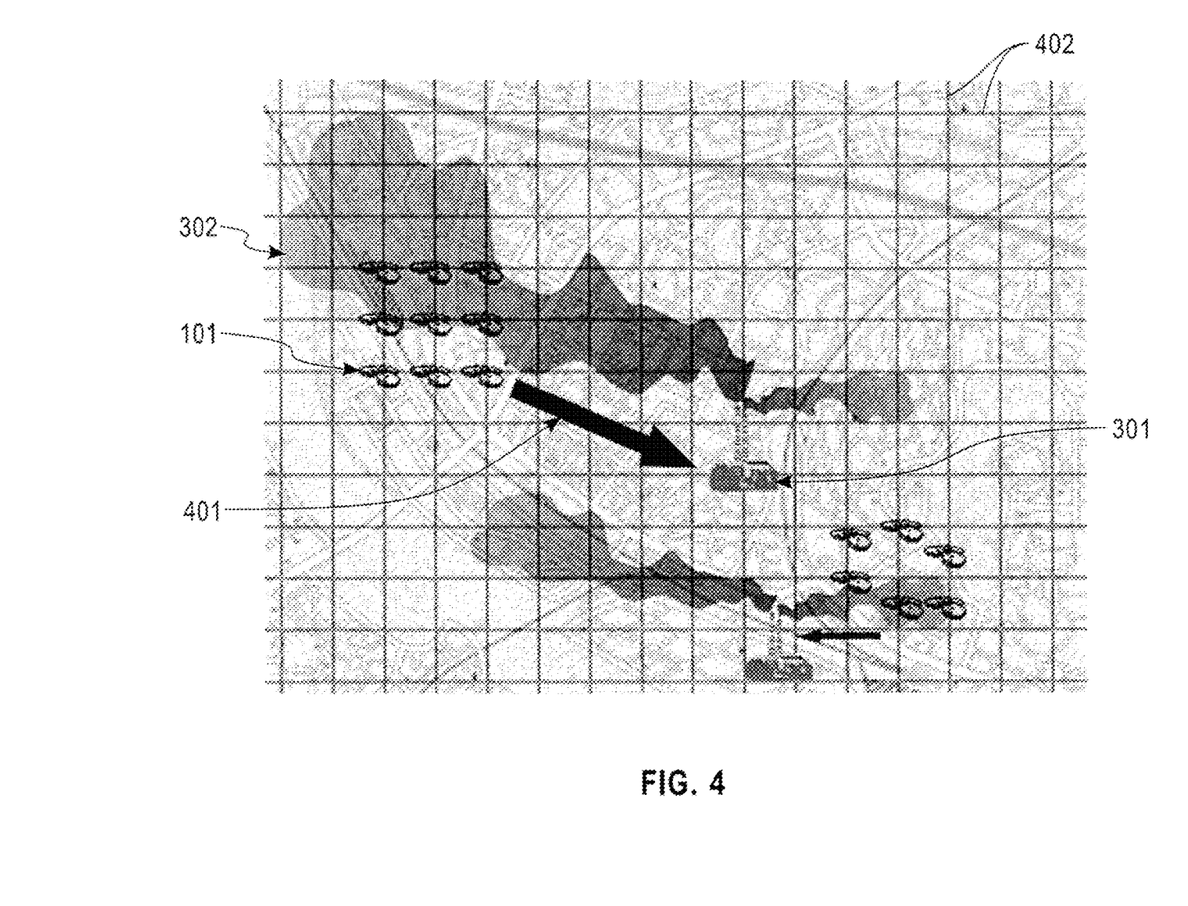
FIG. 4 illustrates an example of automated vehicles tracking a source of pollution by a pollution concentration gradient according to an exemplary embodiment of the present invention.

FIG. 3 illustrates an example of a pollution concentration gradient of emitted pollution according to an exemplary embodiment of the present invention. FIG. 4 illustrates an example of automated vehicles tracking a source of pollution by a pollution concentration gradient according to an exemplary embodiment of the present invention.

Referring to FIGS. 3 and 4, a pollution source 301 may emit pollution and the emitted pollution may have a pollution concentration gradient 302. The pollution concentration gradient 302 may increase across a geographic area when moving closer to the pollution source 301.

The gradient of the concentration according to exemplary embodiments of the present invention may be used by the processor 108 to direct the direction of movement of the automated vehicle 101 to continually and dynamically move toward a direction of higher gradient. The concentration may refer to a concentration of air, noise, water or temperature pollution, for example. Moving toward the higher concentration gradient continually may move the automated vehicle 101 gradually closer to the pollution source 301. The following formula may be employed by the processor 108 to direct the direction of movement of the automated vehicle 101 to continually and dynamically move toward a direction of higher gradient:

$$J = -D\left[\frac{\partial \phi}{\partial X} + \frac{\partial \phi}{\partial Y} + \frac{\partial \phi}{\partial Z}\right]$$

Referring to FIG. 4, the automated vehicle 101 may determine the pollution concentration gradient 302 and may determine a direction of increasing concentration gradient 401. The automated vehicle 101 may move along the direction of increasing concentration gradient 401 toward the pollution source 301 to detect the location of the pollution source 301. The automated vehicle 101 may determine the location of the pollution source 301 according to a grid pattern 402. The grid pattern 402 may be used to geo-locate data points for each detected pollution concentration. That is, the system according to exemplary embodiments of the present invention may plot the pollution concentration for a particular pollution source across a defined geographic area.

A global maximum concentration value and local maximum concentration values may be detected in each segment of the grid pattern 402. The global and local maximum pollution concentrations may be continually detected by predetermined algorithms. For example, the global and local maximum pollution concentrations may be detected by a black box search algorithm, a finite search difference method, a hill climbing method, optimization methods and Nurbs, Splines or surface estimation. However, exemplary embodiments of the present invention are not limited to a particular algorithm, and any algorithm that search for optimal, global maximum, local maximum, local minimum, and global minimum can be used to look for the highest concentration of pollutants in the atmosphere. For example, the automated vehicle 101 according to exemplary embodiments of the present invention may look for Maxima (pollutant concentration) or Minima (air density or O2 concentration).

Figure 5:
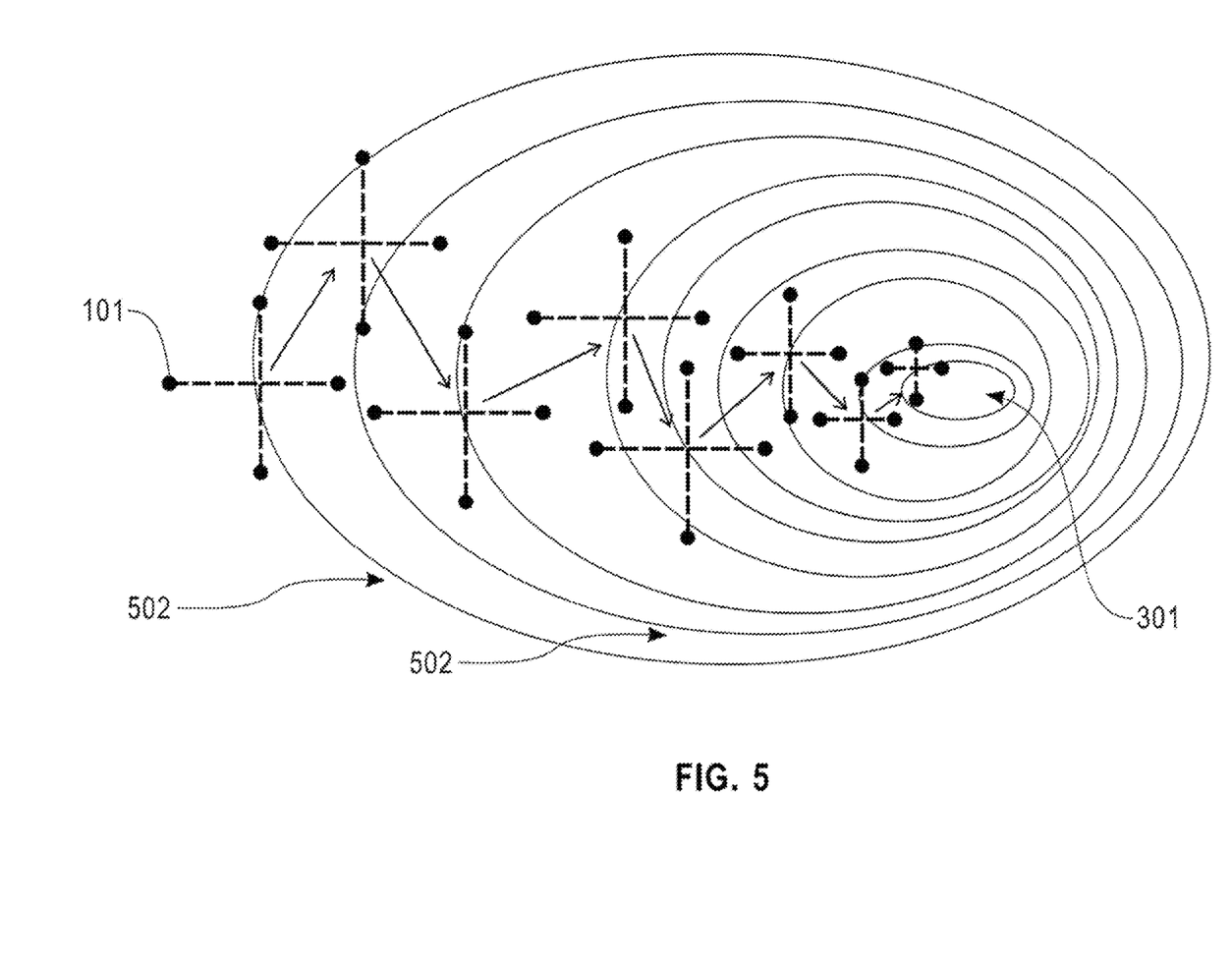
FIG. 5 illustrates an example of a dynamic path of an automated vehicle moving toward a pollution source according to an exemplary embodiment of the present invention.

FIG. 5 illustrates an example of a dynamic path of an automated vehicle moving toward a pollution source according to an exemplary embodiment of the present invention.

Referring to FIG. 5, the automated vehicle 101 may continually adjust its path by detecting the gradient of concentration of the detected pollution. The path of the automated vehicle 101 may be adjusted at a plurality of detection points 502. At each of the plurality of detection points 502 the automated vehicle 101 may detect a plurality of concentration gradients along a plurality of directions with respect to the automated vehicle 101 and the automated vehicle 101 may move toward the highest detected concentration gradient.

The gradient of the concentration according to exemplary embodiments of the present invention may be used by the processor 108 to direct the direction of movement of the automated vehicle 101 to continually and dynamically move toward a direction of higher gradient. The concentration may refer to a concentration of air, noise, water or temperature pollution, for example. Moving toward the higher concentration gradient continually may move the automated vehicle 101 gradually closer to the pollution source 301. The direction of movement of the automated vehicle 101 may be continually adjusted according to a detected concentration gradient in a plurality of directions. For example, the direction of movement may be adjusted at predetermined time points, such as every 30 or 60 seconds, for example. Thus, a number of concentration gradients in a number of potential directions of movement around the automated vehicle 101 may be detected and the direction of movement of the automated vehicle 101 may be adjusted to move toward the highest gradient of concentration and thus toward the pollution source 301.

According to an exemplary embodiment of the present invention, the dynamic and continual directional adjustment of the automated vehicle might not direct the automated vehicle in a straight line toward the pollution source 301 because the direction of movement of the automated vehicle 101 may be adjusted at a series of detection points 502. Thus, while the automated vehicle 101 may make continual progress toward the pollution source 301, the path of the automated vehicle 101 may follow an approximately zig zag pattern, as illustrated, for example, in FIG. 5.

Figure 6:
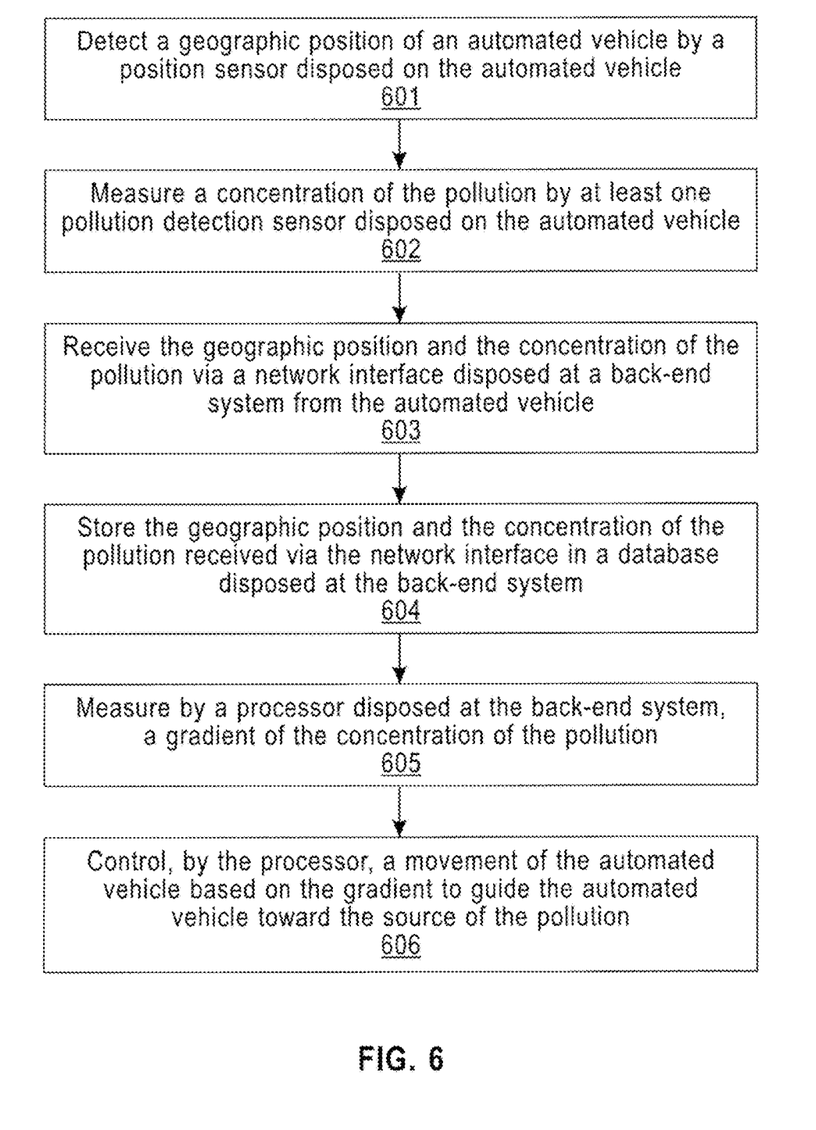
FIG. 6 illustrates a flow chart of a method of detecting a source of pollution according to an exemplary embodiment of the present invention.

FIG. 6 illustrates a flow chart of a method of detecting a source of pollution according to an exemplary embodiment of the present invention.

Referring to FIG. 6, a method of detecting a source of pollution may include detecting a geographic position of the automated vehicle by the position sensor disposed on the automated vehicle 601. A concentration of the pollution may be measured by at least one pollution detection sensor disposed on the automated vehicle 602. The geographic position and the concentration of the pollution may be received via the network interface disposed at a back-end system from the automated vehicle 603. The geographic position and the concentration of the pollution received via the network interface may be stored in the database disposed at the back-end system 604. The method of detection of a source of pollution may include measuring, by a processor disposed at the back-end system, a gradient of the concentration of the pollution 605. The method of detection of a source of pollution may include controlling, by the processor, a movement of the automated vehicle based on the gradient to guide the automated vehicle toward the source of the pollution 606.

According to an exemplary embodiment of the present invention the processor 108 may measure the gradient using a numerical model.

According to an exemplary embodiment of the present invention the processor 108 may measure the gradient in real-time as the automated vehicle 101 moves.

According to an exemplary embodiment of the present invention the method of detection of a source of pollution may include detecting a geographic position of each of a plurality of automated vehicles 101 by a position sensor disposed on each of the plurality of automated vehicles 101. A concentration of the pollution may be measured by at least one pollution detection sensor 103 disposed on each of the plurality of automated vehicles 101. The concentration of the pollution measured by the plurality of automated vehicles 101 may be aggregated. An aggregated gradient of the aggregated concentration of the pollution may be measured. A movement of the plurality of automated vehicles 101 may be controlled based on the aggregated gradient to guide the plurality of automated vehicles 101 toward the source of the pollution.

According to an exemplary embodiment of the present invention the method of detection of a source of pollution may include initially receiving a general location at which the pollution is present from a source other than the automated vehicle 101 and subsequently guiding the automated vehicle 101 to the general location. The movement of the automated vehicle 101 may be controlled based on the gradient to guide the automated vehicle 101 toward the source of the pollution within the general location. For example, the general location of the pollution may be initially received by reports identifying pollution in a particular area, such as complaints by citizens or visitors to a particular location. The general location of the pollution may be initially received from fixed location detectors that are present in a particular area having detectable pollution.

According to an exemplary embodiment of the present invention the method of detection of a source of pollution may include performing, by the processor 108, an inverse geocoding query to detect a company or individual responsible for the source of the pollution. That is, the processor 108 may determine an owner of a parcel of land on which pollution is being emitted or an owner of a particular item of equipment emitting pollution.

Exemplary embodiments of the present invention provide a computer program product for detecting a source of pollution. The computer program product may include a computer readable storage medium having program instructions embodied therewith, the program instructions executable by a processor to cause the processor to detect a geographic position of the automated vehicle 101 by the position sensor 102 disposed on the automated vehicle 101. The program instructions executable by a processor cause the processor to measure a concentration of the pollution by at least one pollution detection sensor disposed on the automated vehicle 101. The program instructions executable by a processor cause the processor to receive the geographic position and the concentration of the pollution via a network interface disposed at a back-end system from the automated vehicle. The program instructions executable by a processor may cause the processor to store the geographic position and the concentration of the pollution received via the network interface in a database disposed at the back-end system 105. The program instructions executable by a processor cause the processor to measure a gradient of the concentration of the pollution and control a movement of the automated vehicle 101 based on the gradient to guide the automated vehicle 101 toward the source of the pollution.

Figure 7:
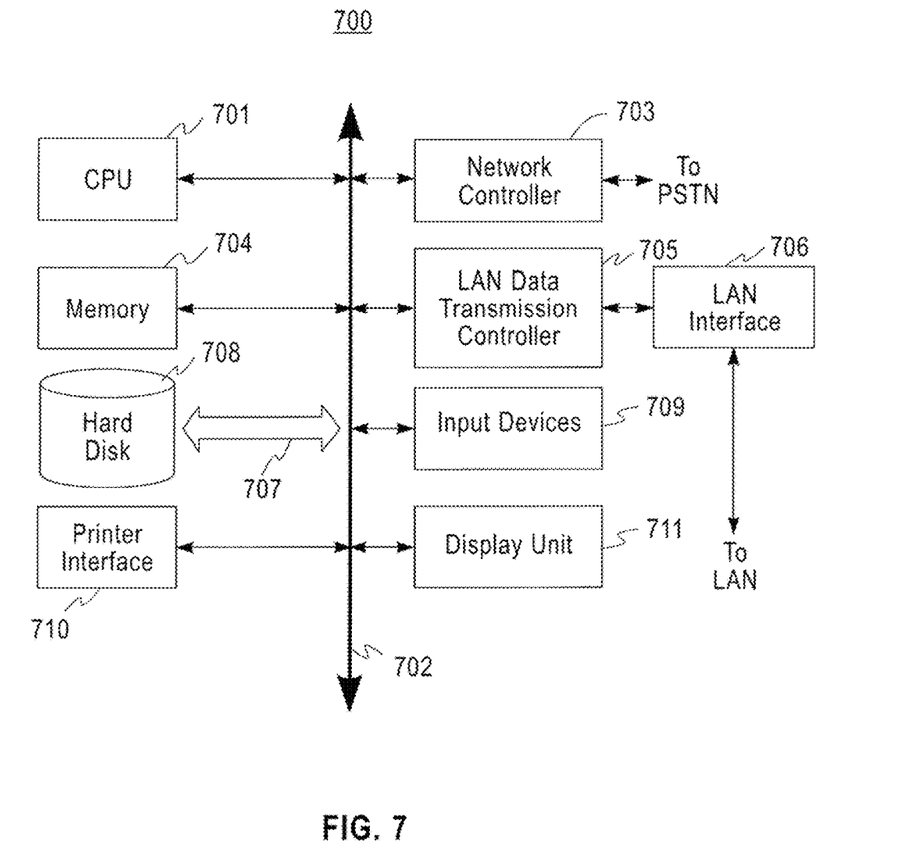
FIG. 7 illustrates an example of a computer system capable of implementing the method according to exemplary embodiments of the present invention.

FIG. 7 illustrates an example of a computer system capable of implementing the methods according to exemplary embodiments of the present invention. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

The computer system referred to generally as system 700 may include, for example, a central processing unit (CPU) 701, random access memory (RAM) 704, a printer interface 710, a display unit 711, a local area network (LAN) data transmission controller 705, a LAN interface 706, a network controller 703, an internal bus 702, and one or more input devices 709, for example, a keyboard, mouse etc. As shown, the system 700 may be connected to a data storage device, for example, a hard disk, 708 via a link 707.

The descriptions of the various exemplary embodiments of the present invention have been presented for purposes of illustration, but are not intended to be exhaustive or limited to the exemplary embodiments disclosed. Many modifications and variations will be apparent to those of ordinary skill in the art without departing from the scope and spirit of the described exemplary embodiments. The terminology used herein was chosen to best explain the principles of the exemplary embodiments, or to enable others of ordinary skill in the art to understand exemplary embodiments described herein.

The flowcharts and/or block diagrams in the figures illustrate the architecture, functionality, and operation of possible implementations of systems, methods, and computer program products according to various exemplary embodiments of the inventive concept. In this regard, each block in the flowchart or block diagrams may represent a module, segment, or portion of instructions, which comprises one or more executable instructions for implementing the specified logical function(s). In alternative implementations, the functions noted in the block may occur out of the order noted in the figures. For example, two blocks shown in succession may, in fact, be executed substantially concurrently, or the blocks may sometimes be executed in the reverse order, depending upon the functionality involved, it will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood that although this disclosure relates to cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

While the present invention has been particularly shown and described with reference to exemplary embodiments thereof, it will be understood by those of ordinary skill in the art that various changes in form and detail may be made therein without departing from the spirit and scope of the present invention as defined by the following claims.

The invention claimed is:

1. A pollution source detection system, comprising:
   an automated vehicle comprising a position sensor that detects a geographic position of the automated vehicle and at least one pollution detection sensor that measures a concentration of pollution at the automated vehicle, wherein the automated vehicle is an automated aerial vehicle, wherein the at least one pollution detection sensor comprises a microphone, the pollution comprises noise pollution, and the microphone detects the concentration of the noise pollution; and
   a back-end system, comprising:
      a network interface that receives the geographic position and the concentration of the pollution from the automated vehicle;
      a database that stores the geographic position and the concentration of the pollution received via the network interface; and
      a processor that measures a gradient of the concentration of the pollution and controls a movement of the automated vehicle based on the gradient to guide the automated vehicle toward a source of the pollution, wherein the gradient includes a range of sounds including relatively low decibel sound and relatively high decibel sound, and wherein the processor controls the movement of the automated vehicle toward the relatively high decibel sound to identify to source of the pollution.

2. The pollution source detection system of claim 1, wherein the processor measures the gradient using a numerical model.

3. The pollution source detection system of claim 1, wherein the processor measures the gradient in real-time as the automated vehicle moves.

4. The pollution source detection system of claim 1, further comprising:
   a plurality of automated vehicles including the automated vehicle,
   wherein each of the plurality of automated vehicles comprises a position sensor that detects a geographic position of the corresponding automated vehicle and at least one pollution detection sensor that measures a concentration of pollution at the corresponding automated vehicle, wherein the at least one pollution detection sensor comprises a microphone, the pollution comprises noise pollution, and the microphone detects the concentration of the noise pollution,
   wherein the processor aggregates the concentration of the pollution measured by the plurality of automated vehicles, measures an aggregated gradient of the aggregated concentration of the pollution, and controls a movement of the plurality of automated vehicles based on the aggregated gradient to guide the plurality of automated vehicles toward the source of the pollution.

5. The pollution detection system of claim 1, wherein the position sensor detects the geographic position in three dimensions.

6. The pollution detection system of claim 1, wherein the network interface is a cellular interface that receives the geographic position and the concentration of the pollution from the automated vehicle via a cellular connection.

7. A computer program product for detecting a source of pollution, the computer program product comprising a computer readable storage medium having program instructions embodied therewith, the program instructions executable by a processor to cause the processor to:
   detect a geographic position of an automated vehicle by a position sensor disposed on the automated vehicle, wherein the automated vehicle is an automated aerial vehicle;
   measure a concentration of the pollution by at least one pollution detection sensor disposed on the automated vehicle, wherein the at least one pollution detection sensor comprises a microphone, the pollution comprises noise pollution, and the microphone detects the concentration of the noise pollution;
   receive the geographic position and the concentration of the pollution via a network interface disposed at a back-end system from the automated vehicle;
   store the geographic position and the concentration of the pollution received via the network interface in a database disposed at the back-end system;
   measure a gradient of the concentration of the pollution, wherein the gradient includes a range of sounds including relatively low decibel sound and relatively high decibel sound; and
   control a movement of the automated vehicle based on the gradient to guide the automated vehicle toward the source of the pollution to identify to source of the pollution.

8. The pollution detection system of claim 1, wherein the network interface initially receives a general location at which the pollution is present from a source other than the automated vehicle, and the processor subsequently guides the automated vehicle to the general location and controls the movement of the automated vehicle based on the gradient to guide the automated vehicle toward the source of the pollution within the general location.

9. The pollution detection system of claim 1, wherein the processor performs an inverse geocoding query to detect a company or individual responsible for the source of the pollution.

10. A method of detecting a source of pollution, comprising:
    detecting a geographic position of an automated aerial vehicle by a position sensor disposed on the automated aerial vehicle;
    measuring a concentration of the pollution by at least one pollution detection sensor disposed on the automated aerial vehicle, wherein the at least one pollution detection sensor comprises a microphone, the pollution comprises noise pollution, and the microphone detects the concentration of the noise pollution;
    receiving the geographic position and the concentration of the pollution via a network interface disposed at a back-end system from the automated aerial vehicle;

storing the geographic position and the concentration of the pollution received via the network interface in a database disposed at the back-end system;

measuring, by a processor disposed at the back-end system, a gradient of the concentration of the pollution wherein the gradient includes a range of sounds including relatively low decibel sound and relatively high decibel sound; and controlling, by the processor, a movement of the automated aerial vehicle based on the gradient to guide the automated aerial vehicle toward the source of the pollution to identify to source of the pollution.

11. The method of claim 10, wherein the processor measures the gradient using a numerical model.

12. The method of claim 10, wherein the processor measures the gradient in real-time as the automated aerial vehicle moves.

13. The method of claim 10, further comprising:

detecting a geographic position of each of a plurality of automated vehicles, including the automated vehicle, by a position sensor disposed on each of the plurality of automated vehicles;

measuring a concentration of the pollution by at least one pollution detection sensor disposed on each of the plurality of automated vehicles, wherein the at least one pollution detection sensor comprises a microphone, the pollution comprises noise pollution, and the microphone detects the concentration of the noise pollution;

aggregating the concentration of the pollution measured by the plurality of automated vehicles;

measuring an aggregated gradient of the aggregated concentration of the pollution; and controlling a movement of the plurality of automated vehicles based on the aggregated gradient to guide the plurality of automated vehicles toward the source of the pollution.

14. The method of claim 10 further comprising:

initially receiving a general location at which the pollution is present from a source other than the automated vehicle;

subsequently guiding the automated vehicle to the general location; and controlling the movement of the automated vehicle based on the gradient to guide the automated vehicle toward the source of the pollution within the general location.

15. The method of claim 10, further comprising:

performing, by the processor, an inverse geocoding query to detect a company or individual responsible for the source of the pollution.

* * * * *